United States Patent [19]

Yasaburgo et al.

[11] Patent Number: 4,714,611

[45] Date of Patent: Dec. 22, 1987

[54] STABLE COMPOSITION OF GAMMA-INTERFERON

[75] Inventors: Akagi Yasaburgo, Takatsuki; Miura Yasumoto, Kawanishi; Hoshino Tetsuo, Toyonka, all of Japan

[73] Assignee: Takeda Chemical Industries, Ltd., Osaka, Japan

[21] Appl. No.: 693,669

[22] Filed: Jan. 22, 1985

[30] Foreign Application Priority Data

Jan. 23, 1984 [JP] Japan ................... 59-10857
Jan. 9, 1985 [JP] Japan ................... 60-2585

[51] Int. Cl.$^4$ .................. A61K 45/02; C07K 15/26
[52] U.S. Cl. .................... 424/85; 435/68; 435/811; 530/351
[58] Field of Search ........ 424/85; 260/112 R; 435/68; 530/351

[56] References Cited

U.S. PATENT DOCUMENTS

| | | | |
|---|---|---|---|
| 4,041,152 | 8/1977 | Chany et al. | 424/85 |
| 4,100,150 | 7/1978 | Cartwright | 260/112 |
| 4,314,935 | 8/1980 | Uemura et al. | 424/85 |
| 4,465,622 | 8/1984 | Nohuhara et al. | 424/85 |

FOREIGN PATENT DOCUMENTS 80879 6/1983 European Pat. Off. .
123291 10/1984 European Pat. Off. .

OTHER PUBLICATIONS

Gray et al., Naline, vol. 275, pp. 503–508, 1982.
Sedmak et al., Methods in Enzymology, vol. 78, pp. 591–595.
Central Patent Index, Abstract Journal, Section B, No. 53236B/29 the Abstract of Japanese Patent Publication (laid open) No. 70419/79.
Central Patent Index, Abstract Journal, Section B, No. 28261D/16 the Abstract of Japanese Patent Publication (laid open) No. 20519/81.

Primary Examiner—Blondel Hazel
Attorney, Agent, or Firm—David G. Conlin; Linda M. Buckley

[57] ABSTRACT

A stable human γ-interferon composition is produced by adding dextran and/or hydroxyethylstarch to an aqueous human γ-interferon solution freezing the resulting solution and, if desired, drying the resulting frozen solution under reduced pressure.

25 Claims, 2 Drawing Figures

Fig. 1

```
  1
Cys Tyr Cys Gln Asp Pro Tyr Val Lys Glu
                                     20
Ala Glu Asn Leu Lys Lys Tyr Phe Asn Ala

Gly His Ser Asp Val Ala Asp Asn Gly Thr
                                     40
Leu Phe Leu Gly Ile Leu Lys Asn Trp Lys

Glu Glu Ser Asp Arg Lys Ile Met Gln Ser
                                     60
Gln Ile Val Ser Phe Tyr Phe Lys Leu Phe

Lys Asn Phe Lys Asp Asp Gln Ser Ile Gln
                                     80
Lys Ser Val Glu Thr Ile Lys Glu Asp Met

Asn Val Lys Phe Phe Asn Ser Asn Lys Lys
                                    100
Lys Arg Asp Asp Phe Glu Lys Leu Thr Asn

Tyr Ser Val Thr Asp Leu Asn Val Gln Arg
                                    120
Lys Ala Ile His Glu Leu Ile Gln Val Met

Ala Glu Leu Ser Pro Ala Ala Lys Thr Gly
                                    140
Lys Arg Lys Arg Ser Gln Met Leu Phe Arg
                        146
Gly Arg Arg Ala Ser Gln
```

STABLE COMPOSITION OF GAMMA-INTERFERON

This invention relates to a γ-interferon composition.

Human interferons are classified into three types, namely α, β and γ types. Interferons of the α and β types are relatively stable and submitted to clinical use mostly in the parenteral dosage forms, and are now under considerably advanced, systematic, clinical studies. On the other hand, γ-interferon (hereinafter sometimes abbreviated as IFN-γ) is very unstable and, in aqueous solutions, its activity is readily reduced during storage, freezing or lyophilization. This fact renders it very difficult to obtain a stable composition suitable for clinical applications and therefore constitutes a serious obstacle to the clinical use of IFN-γ. IFN-γ has the most potent antitumor activity among interferons and is expected to have wide clinical applications. The present inventors have established a method for producing stable IFN-γ compositions which do not lose any substantial IFN-γ activity even after freezing and lyophilization.

Thus, the invention provides a human γ-interferon composition frozen or lyophilized in the presence of dextran and/or hydroxyethylstarch, a method of producing the same and a method of stabilizing the human γ-interferon.

As the IFN-γ to be used in accordance with the invention, there may be used any human-derived IFN-γ which is either a natural product or a product by the recombination technique. For instance, there may be used a product obtained by concentration naturally occurring human IFN-γ, i.e. natural IFN-γ (nIFN-γ) and a human IFN-γ-containing material produced by cultivating a human IFN-γ-producing microorganism obtained in turn by the gene manipulation technology [cf. European Patent Publication No. 0 089 676; Nucleic Acids Research, 10, 2,487–2,501 (1982); Nature, 295, 503–508 (1982); Nucleic Acids Research, 10, 3605–3615 (1982)], i.e. recombinant IFN-γ (rIFN-γ). More concretely, the above-mentioned rIFN-γ includes polypeptide consisting of 146 amino acids, for example, of the sequence shown in FIG. 1 and various fragments of the polypeptide, such as N terminal portion-deficient species, i.e. lacking not more than four amino acids of the N terminal part of the polypeptide and C terminal portion-deficient species which are cleaved at a site not earlier than the 131st amino acid residue of the polypeptide or the N terminal portion-deficient species. Furthermore, the rIFN-γ includes a polypeptide the cystein residues of the polypeptide being replaced by serine or threonine.

The polypeptide consisting of 146 amino acids and the N terminal portion-deficient species lacking

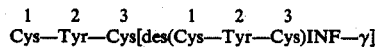

are preferably used among others.

In particular, the use of an aqueous solution containing human IFN-γ in high concentration which is obtainable by the gene recombination technique is advantageous.

The specific activity of human IFN-γ should preferably be $1 \times 10^5$ to $1 \times 10^7$ international units/mg (IU/mg) and the aqueous IFN-γ solution should preferably have an activity of $1 \times 10^2$ to $1 \times 10^7$ IU/ml, more preferably $1 \times 10^4$ to $1 \times 10^7$ IU/ml.

As the dextran and hydroxyethylstarch, there may be used commercially available products. However, for clinical application of the composition of the invention, they should preferably be of almost the same grade as those which are used in preparing plasma substitutes for parenteral administration. The use of dextran having an average molecular weight of 10,000–100,000, preferably 40,000–70,000, and hydroxyethylstarch having an average molecular weight of 10,000–200,000, preferably 20,000–60,000 or 200,000, is advantageous.

The dextran and hydroxyethylstarch should preferably be contained in the aqueous IFN-γ solution in an amount of not less than 1 mg, more preferably 3 mg to 50 mg, per milliliter of said solution.

In addition to the above dextran and/or hydroxyethylstarch, human serum albumin (HSA) can be incorporated into the composition according to the invention. When incorporated, HSA is preferably added in an amount of 2–20 mg per milliliter of the aqueous IFN-γ solution.

The composition according to the invention may also contain a reducing sulfur compound when human IFN-γ therein has cysteine residue. Said reducing sulfur compound includes glutathione (reduced form), thioctic acid, cysteine, N-acetylcysteine, N-acetylhomocysteine, thiodiglycol, thioethanolamine, monothioglycerol, dithiothreitol and thioalkanoic acids of 1–7 carbon atoms. Among them glutathione (reduced form) is preferred. When allowed to coexist, such reducing sulfur compounds should preferably be used in an amount of not less than 0.1 mg, more preferably 0.5–10 mg, per milliliter of the aqueous IFN-γ solution.

The further addition of one or more stabilizing agents selected from among amino acids, such as glycine, glutamic acid and α-alanine, physiologically acceptable salts and derivatives thereof, monosaccharides, such as glucose, fructose, mannose and galactose, and disaccharides, such as sucrose, maltose and lactose, will result in a further increase in stability and, accordingly, these substances may optionally be incorporated.

Among the above stabilizing agents, sucrose is preferred. In incorporating sucrose, its amount should preferably be 10–50 mg per milliliter of the aqueous IFN-γ solution.

The composition may further contain a surfactant, such as Tween 20, a buffer, an isotonizing agent, and others.

The human IFN-γ composition according to the invention, which is a frozen product or a lyophilizate, can be produced, for example, by the following method.

To an aqueous solution containing human IFN-γ in a concentration of $1 \times 10^2$ to $1 \times 10^7$ IU/ml, there is added dextran and/or hydroxyethylstarch in an amount (total amount when both are used) sufficient to make a concentration of not less than 1 mg/ml, preferably 3–50 mg/ml. The above-mentioned HSA, sucrose and other agents may optionally be added. The above aqueous IFN-γ solution may contain not less than 0.1 mg/ml, preferably 0.5–10 mg/ml, of reducing sulfur compound and/or a trace amount of surfactant, or a reducing sulfur compound and/or surfactant may be added anew to said solution as in the case of the above-mentioned stabilizing agents.

The frozen human IFN-γ composition according to the invention can be produced, for example, by freezing the above aqueous solution generally at −80° to −30°

C. Said frozen composition should preferably be stored at −80° to −10° C.

The lyophilized human IFN-γ composition according to the invention can be produced, for example, by drying the above frozen composition under reduced pressure of not more than 0.1 torr at a controlled temperature from frozen temperature (initiation) till 30° C. (end). Said lyophilized composition also be obtained by first thawing the frozen composition mentioned above, transferring the thus obtained aqueous solution to an appropriate vial, and then freezing and drying the solution under reduced pressure in the conventional manner.

In producing a lyophilized human IFN-γ composition according to the invention as an injectable preparation, a preferred process comprises a series of steps such as sterile filtration, aseptic filling into vials and lyophilization.

The frozen or lyophilized human IFN-γ composition according to the invention is useful since the activity decrease during lyophilization or subsequent storage is slight. The lyophilized composition is obtained in the form of a stabilized human IFN-γ-containing solid and can advantageously be used especially as a parenteral preparation.

When the lyophilized human IFN-γ composition according to the invention is used as an injectable preparation, the lyophilized composition is dissolved, generally just prior to use, in 1–100 ml per vial of distilled water for injection, physiological saline or injectable glucose solution. The composition may also be used in the form of an occular, auricular or nasal preparation prepared by using an appropriate carrier, excipient or diluent.

The frozen or lyophilized human IFN-γ composition according to the invention is stable, has low toxicity and can be used in the same manner and for the same purposes as the known human IFN-γ products.

The IFN-γ activity as described herein in terms of antiviral activity in international units (IU) or units (U) was determined in the following manner.

IU: An international standard IFN-γ having an established potency in units and a test sample were assayed by the Sindbis virus-induced cytopathic effect inhibition test in the human amnion-derived FL cell line, followed by calculation of the potency in question based on the ratio between the data obtained.

U: An international standard IFN-α having an established potency in units and a leukocyte-derived crude IFN-γ were assayed by the vesicular stomatitis virus (VSV)-induced cytopathic effect inhibition test in the human amnion-derived FL cell line. The potency of the leukocyte-derived crude IFN-γ was determined by comparing the potency data obtained. Using the crude IFN-γ as a standard, the IFN-γ potency of a test sample was determined by assaying the sample, always in parallel with said standard IFN-γ, for the antiviral activity by the VSV-induced cytopathic effect inhibition test in the human amnion-derived WISH cell line, followed by potency calculation based on the potency ratio found.

The protein content in solution was calculated on the assumption that E: 280 nm=1.0 is equivalent to 1 mg.

The thus-obtained international unit (IU) value and unit (U) value were approximately in the following relation:

$$IU \approx \tfrac{1}{2} U$$

BRIEF DESCRIPTION OF THE DRAWINGS

FIG. 1 illustrates the amino acid sequence of human IFN-γ consisting of 146 amino acids.

Figure 2:
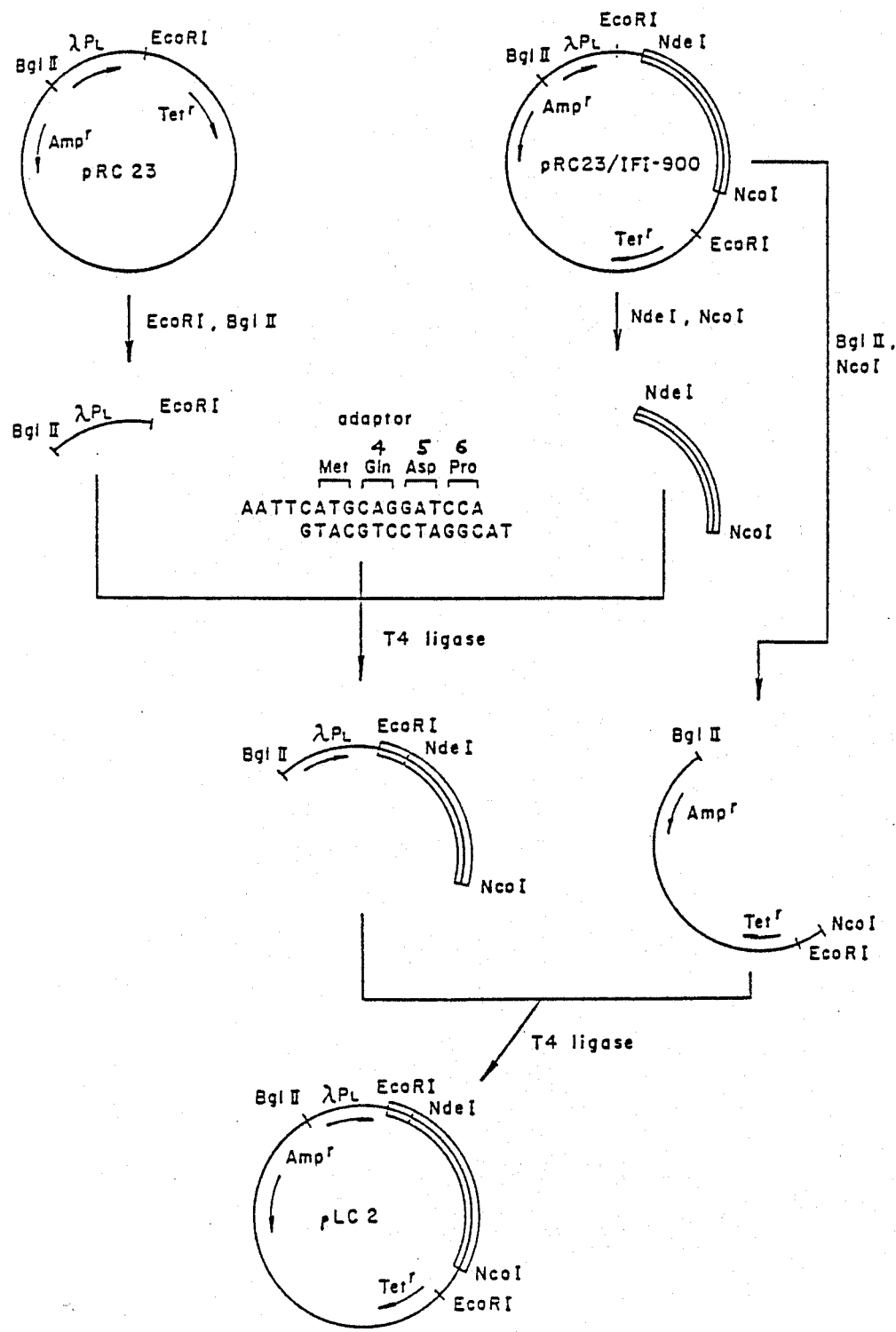
FIG. 2 illustrates the construction scheme of the expression plasmid pLC2 disclosed in Reference Example 4(i).

The following examples illustrate the invention in more detail. It is to be noted, however, that they are by no means limitative of the present invention.

The human IFN-γ used in the examples was, unless otherwise specified, a preparation produced by the method described in Reference Example 2(II). In Example 6, the human IFN-γ prepared by the method described in Reference Example 3 was used and in Examples 8, 9 and 10,

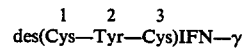

prepared by the method described in Reference Example 5 was used.

EXAMPLE 1

To 1 ml of an aqueous human IFN-γ solution having an IFN-γ concentration of $2 \times 10^5$ U/ml and containing 3 mg of glutathione, were added 60 mg of dextran (average molecular weight 70,000) and 0.5 ml of distilled water for injection, followed by sterile filtration. The thus-obtained aqueous solution (1.5 ml) was placed in a vial, frozen at −30° C. and lyophilized. The lyophilizate was reconstituted with distilled water for injection and assayed for the IFN-γ potency.

As a control, 50 mg of D-mannitol, which is generally used in lyophilization, was added, in place of dextran, to the aqueous IFN-γ solution. The solution was then lyophilized in the same manner.

The percentage residual potency as calculated based on the potency of the human IFN-γ solution before lyophilization was 61% for the control and 94% for the lyophilizate according to the invention.

EXAMPLE 2

To 1 ml of an aqueous human IFN-γ solution having an IFN-γ concentration of $7 \times 10^5$ U/ml and containing 3 mg of glutathione, were added 30 mg of hydroxyethylstarch (average molecular weight 200,000) and 0.5 ml of distilled water for injection, followed by sterile filtration. The thus-obtained aqueous solution (1.5 ml) was placed in a vial and frozen (−30° C.) or lyophilized. The frozen product was thawed, and the lyophilizate was reconstituted with distilled water for injection, and each aqueous solution obtained was assayed for the IFN-γ potency.

The percentage residual potency based on the potency of the human IFN-γ solution before freezing or lyophilization was 111% for the frozen product (−30° C.), and 117% for the lyophilizate. These data were indicative of the stability of the products. The percentage residual potency after two weeks of storage at −30° C. (frozen product) or at 40° C. (lyophilizate) as calculated based on the potency at the start of storage was 121% and 107%, respectively.

EXAMPLE 3

The procedure of Example 2 was followed except that 10 mg of sodium glutamate was additionally added.

The percentage residual potency was 83% for the lyophilizate, and 105% for the frozen product after two-week storage at −30° C. The percentage residual potency for the lyophilizate stored at 40° C. for 2 weeks as compared with the potency at the start of storage was 105%. Thus all the data indicated the stability of the products.

EXAMPLE 4

The procedure of Example 1 was followed except that the amount of dextran (average molecular weight 70,000) was reduced to 30 mg and that 5 mg of human serum albumin was further added.

The percentage residual potency was 78% for the lyophilizate, and 90% for the frozen product stored at −30° C. for 2 weeks. For the lyophilizate stored at 40° C. for 2 weeks, the percentage residual potency based on the potency at the start of storage was 112%. The stability of the products was thus established.

EXAMPLE 5

An IFN-γ solution prepared in accordance with Example 2 except for the addition of 51 mg of sucrose was lyophilized. The lyophilizate was reconstituted with distilled water for injection and assayed for the human IFN-γ potency.

The percentage residual potency based on the potency of the human IFN-γ solution before lyophilization was 99%.

EXAMPLE 6

To 1 ml of the aqueous human IFN-γ solution having an IFN-γ concentration of $1.6 \times 10^6$ IU/ml and containing 3 mg of glutathione as obtained by the procedure of Reference Example 3, there were added 30 mg of hydroxyethylstarch (average molecular weight 200,000) and 0.5 ml of distilled water for injection, followed by sterile filtration. The thus-obtained aqueous solution (1.5 ml) was lyophilized in a vial.

The lyophilizate was reconstituted with distilled water for injection and assayed for the human IFN-γ potency.

The percentage residual potency based on the potency of the aqueous solution before lyophilization was 88%.

EXAMPLE 7

A 1-ml portion of an aqueous human IFN-γ solution having a concentration of $3.0 \times 10^5$ IU/ml prepared with preliminarily nitrogen-substituted distilled water for injection and an aqueous solution (1.5 ml) containing 30 mg of hydroxyethylstarch were combined and lyophilized in a vial.

The lyophilizate was reconstituted with distilled water for injection and assayed for the IFN-γ potency.

The residual potency was 74% based on the potency of the aqueous solution before lyophilization.

EXAMPLE 8

To 1 ml of the aqueous solution containing $2.5 \times 10^6$ IU/ml of

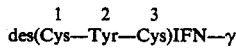

des(Cys¹—Tyr²—Cys³)IFN—γ as obtained by the procedure of Reference Example 5, there were added 30 mg of dextran (average molecular weight 70,000) and 0.5 ml of distilled water for injection, followed by sterile filtration. The thus obtained aqueous solution (1.5 ml) was lyophilized in a vial.

The lyophilizate was reconstituted with distilled water for injection and assayed for the human IFN-γ potency.

The percentage residual potency based on the potency of the aqueous solution before lyophilization was 92%.

EXAMPLE 9

The procedure of Example 8 was followed except that 30 mg of hydroxyethylstarch (average molecular weight 200,000) was added rather than 30 mg of dextran.

The percentage residual potency based on the potency of the aqueous solution before lyophilization was 95%.

EXAMPLE 10

The procedure of Example 9 was followed except that 10 mg of sodium glutamate was further added.

The percentage residual potency based on the potency of the aqueous solution before lyophilization was 104%.

REFERENCE EXAMPLE 1

The strain RRI (pRK 248 cIts, pRC 231/IFI-900) carrying the human IFN-γ expression gene as described in Example 8 in Japanese unexamined patent publication No. 189,197/1983 was cultivated in M9-glucose medium at 30° C. until the cell concentration reached $3-4 \times 10^8$ cells/ml. Glucose and casamino acid were then added in concentration of 1.0% and 0.5%, respectively. After an hour of induction at 42° C., the culture was centrifuged and the cells thus collected were frozen and stored.

REFERENCE EXAMPLE 2

(I) To 1,000 g of the forzen cells obtained in Reference Example 1 was added 3,000 ml of 100 mM Tris hydrochloride buffer (pH 7.0) containing 7M guanidine hydrochloride and 2 mM phenylmethylsulfonyl fluoride. The mixture was stirred at 4° C. for 1 hour and centrifuged (17,000 rpm/30 minutes). The clear and transparent supernatant thus obtained was diluted 70-fold with a buffer comprising 137 mM sodium chloride, 27 mM potassium chloride, 8 mM disodium hydrogen phosphate and 147 mM potassium dihydrogen phosphate (hereinafter abbreviated as PBS). The resultant precipitate was removed using a Sharples centrifuge (10,000 rpm). The supernatant obtained (220 liters) was concentrated to 15 liters using a Pericon membrane filter (Millipore Corp.; cut-off molecular weight: 10,000). The concentrate was allowed to stand at 4° C. overnight and the resultant precipitate was removed by further centrifugation on a Sharples centrifuge. A preliminarily packed antibody column [Ab (Mo γ2-11.1); $5 \times 30$ cm; refer to the specification Japanese patent application No. 176091/1983 (filed on Sept. 22, 1983)] was loaded with the above supernatant at a flow rate of 1,000 ml/hour. Thereafter, washing solutions, namely 2,500 ml of PBS, 5,000 ml of 10 mM phosphate buffer (pH 7.0) containing 1M sodium chloride and 0.1% Tween 20, 2,500 ml of PBS and 2,500 ml of 20 mM phosphate buffer (pH 7.0) containing 0.5M guanidine hydrochloride, were passed through the column in that order, followed by elution with a 20 mM phosphate buffer (pH 7.0) containing 2M guanidine hydrochloride.

There was collected 500 ml of eluate fraction having antiviral activity.

(II) Glutathione (reduced form) was added, in an amount to give a concentration of 10 mM, to the eluate fraction (420 ml) obtained in Reference Example 2(I). A Sephacryl S-200 (pharmacia) column (9×100 cm) equilibrated in advance with a 25 mM acetate buffer (pH 6.0) containing 1 mM ethylenediaminetetraacetate, 150 mM sodium chloride, 10 mM glutathione (reduced form) and 2M guanidine hydrochloride was loaded with the above human IFN-γ solution (420 ml), followed by elution with the same buffer. A monomer eluate fraction (450 ml) was thus collected. This treatment gave human IFN-γ (0.410 mg/ml) having a specific activity of $3.4 \times 10^6$ IU/mg.

REFERENCE EXAMPLE 3

To a 450 ml of the IFN-γ (monomeric)-containing eluate obtained in Reference Example 2(II), there was added 25 ml of a 25 mM acetate buffer (pH 6.0) containing 10 mM glutathione (reduced form), 150 mM sodium chloride, 0.5M guanidine hydrochloride and 0.01% Tween 20, followed by stirring. Thus was prepared a low concentration solution with a protein content of 0.05 mg/ml. A Sephadex G-25 column (14×100 cm) equilibrated in advance with a 25 mM acetate buffer (pH 6.0) containing 10 mM glutathione (reduced form), 150 mM sodium chloride and 0.01% Tween 20 was loaded with the above solution and elution was performed with the same buffer to give a guanidine hydrochloride-free, IFN-γ-containing eluate fraction (3,180 ml; protein content: 55.8 mg). The protein concentration of this solution was 0.049 mg/ml. The protein recovery was 84.8%, and the specific IFN-γ activity was $3.5 \times 10^6$ IU/mg of protein.

The solution thus obtained was aged at 4° C. for 48 hours and, then, concentrated to 159 ml by ultrafiltration using Diaflo PM-10, 43 mm φ (Amicon's ultrafiltration membrane). The concentrate was clear and transparent and the protein concentration was 0.92 mg/ml. The protein recovery was 93.9% (146.3 mg). The specific IFN-γ activity was $6.8 \times 10^6$ IU/mg of protein.

REFERENCE EXAMPLE 4

Production of

(i) Transformant production

The IFN-γ expression plasmid pRC23/IFI-900 [cf. Example 7 of the specification for a patent application under EPC as laid open under No. 0089676] was digested with the restriction enzymes NdeI and NcoI, and a 710 bp NdeI-NcoI DNA fragment (A) containing the IFN-γ gene region was isolated. Separately, the plasmid pRC23 was digested with the restriction enzymes BglII and EcoRI, and a 265 bp DNA fragment (B) containing the λP$_L$ promoter was isolated. The fragments (A) and (B) and the chemically synthesized, protein synthesis start codon-containing oligonucleotide

AATTCATGCAGGATCCA
GTACGTCCTAGGTAT were joined together using T4 DNA ligase, with the NdeI and EcoRI cohesive ends as the sites of joining. The DNA fragment thus obtained was joined to the plasmid pRC23/IFI-900 after treatment with NcoI and BglII, to thereby construct an expression plasmid, pLC2, coding for the

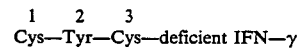

polypeptide (FIG. 2). This plasmid pLC2 was used for transforming *Escherichia coli* RRI(pRK248 cIts) by the method of Cohen et al. [P.N.A.S. (USA), 69, 2110 (1972)] to give a transformant, *Escherichia coli* (=*E. coli*) PRI(pLC2, pRK248 cIts).

(ii) Transformant cultivation

The strain *E. coli* RRI(pLC2, pRK248 cIts) carrying the plasmid constructed in (i) above was shake-cultured at 35° C. in 50 ml of a liquid medium containing 1% Bactotryptone, 0.5% yeast extract, 0.5% sodium chloride and 7 μg/ml tetracycline. The culture broth was transferred to 2.5 liters of M9 medium containing 0.5% casamino acids, 0.5% glucose and 7 μg/ml tetracycline, and grown at 35° C. for 4 hours and then at 42° C. for 3 hours. Cells were harvested by centrifugation and stored at −80° C.

(iii) Purification

In 22 ml of 0.1M Tris-hydrochloride buffer (pH 7.0) containing 7M guanidine hydrochloride and 2 mM phenylmethylsulfonyl fluoride, there were suspended 7.1 g of frozen cells obtained in the same manner as mentioned above in (ii). The suspension was stirred at 4° C. for 1 hour and then centrifuged at 10,000×g for 30 minutes to give 24 ml of a supernatant. This supernatant was diluted by adding 300 ml of PBS and was applied to an antibody column (Moγ2-11.1, column capacity 15 ml) at a flow rate of 1 ml/minute. Thereafter, the column was washed with 60 ml of 20 mM sodium phosphate buffer (pH 7.0) containing 0.5M guanidine hydrochloride and then eluted with 45 ml of 20 mM sodium phosphate buffer (pH 7.0) containing 2M guanidine hydrochloride, to give 25 ml of an antivirally active fraction. This fraction (25 ml) was applied to a Sephacryl S-200 (Pharmacia) column (2.6×94 cm; column capacity 500 ml) equilibrated in advance with 25 mM ammonium acetate buffer (pH 6.0) containing 1 mM ethylenediaminetetraacetic acid, 0.15M sodium chloride, 10 mM cysteine and 2M guanidine hydrochloride, and eluted with the same buffer to give 40 ml of an antivirally active fraction.

The thus obtained

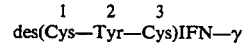

weighed 7.0 mg and had a specific activity of $2.7 \times 10^6$ IU/mg.

REFERENCE EXAMPLE 5

To 2.2 ml of eluate (protein content: 0.331 mg/ml) containing

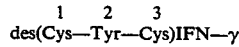

obtained in Reference Example 4(iii), there was added 8 volumes of a 25 mM acetate buffer diluent (pH 6.0) containing 150 mM sodium chloride and 2M guanidine hydrochloride followed by stirring. Thus was prepared a low concentration solution. A Sephadex G-25 column (2.6×15 cm) equilibrated in advance with a 25 mM acetate buffer (pH 6.0) containing 150 mM sodium chloride was loaded with the above solution and elution was performed with the same buffer to give a guanidine hydrochloride-free $$\text{des}(\overset{1}{\text{Cys}}-\overset{2}{\text{Tyr}}-\overset{3}{\text{Cys}})\text{IFN}-\gamma\text{-containing}$$

eluate fraction (30 ml). The protein concentration of this solution was 0.022 mg/ml and the solution was clear and transparent.

This eluate fraction was aged at 4° C. for 24 hours and, then, concentrated to 0.68 ml by ultrafiltration using Diaflo YM-10, 25 mm φ (Amicon's ultrafiltration, membrane, and filtered using a filter (0.2 μm) to obtain 0.68 ml of clear and transparent solution. The protein concentration was 0.670 mg/ml. The protein recovery was 63%.

What is claimed is:

1. A human γ-interferon composition frozen or lyophilized in the presence of an aqueous solution comprising 3 to 50 mg/ml dextran or hydroxyethylstarch or a combination thereof.

2. The composition according to claim 1, wherein the human γ-interferon is a recombinant human γ-interferon.

3. The composition according to claim 2, wherein the recombinant human γ-interferon is derived from highly concentrated aqueous human recombinant γ-interferon solution.

4. The composition according to claim 2, wherein the recombinant human γ-interferon has a specific activity of $1\times10^5$ to $1\times10^7$ IU/mg.

5. The composition according to claim 1, wherein the human γ-interferon is in a concentration of $1\times10^2$ to $1\times10^7$ IU/ml as an aqueous solution.

6. The composition according to claim 1, which contains dextran.

7. The composition according to claim 6, wherein the dextran has an average molecular weight of 10,000 to 100,000.

8. The composition according to claim 1, which contains hydroxyethylstarch.

9. The composition according to claim 8, where the hydroxyethylstarch has an average molecular weight of 10,000 to 200,000.

10. The composition according to claim 1, which further contains human serum albumin.

11. The composition according to claim 1, which further contains disaccharide.

12. The composition according to claim 11, wherein the disaccharide is sucrose.

13. The composition according to claim 1, which further contains an amino acid.

14. The composition according to claim 1, which further contains a reducing sulfur compound.

15. The composition according to claim 14, wherein the reducing sulfur compound is glutathione (reduced form).

16. The composition according to claim 14, wherein the reducing sulfur compound is in a concentration of 0.5 to 100 mg/ml as an aqueous solution.

17. The composition according to claim 1, which is in a frozen form.

18. The composition according to claim 1, which is in a lyophilized form.

19. A method of producing a human γ-interferon composition, which comprises adding 3 to 50 mg/ml dextran or hydroxyethylstarch or a combination thereof to an aqueous human γ-interferon solution, freezing the resulting solution to produce the frozen composition on drying the frozen composition under reduced pressure to produce the lyophilized composition.

20. The method according to claim 19, wherein the aqueous human γ-interferon is in a concentration of $1\times10^2$ to $1\times10^7$ IU/ml.

21. The method according to claim 19, wherein hydroxyethylstarch is added to the solution.

22. The method according to claim 21, wherein hydroxyethylstarch is added to the solution in a concentration of 3 to 50 mg/ml.

23. The method according to claim 19, wherein the freezing is conducted at a temperature of −80° to −30° C.

24. The method according to claim 19, wherein drying is conducted under reduced pressure of not more than 0.1 torr.

25. A method for stabilizing human γ-interferon, which comprises adding 3 to 50 mg/ml dextran or hydroxyethylstarch or a combination thereof to an aqueous human γ-interferon solution, freezing the resulting solution and, if desired, drying the resulting frozen solution under reduced pressure.

* * * * *